US012760282B2

(12) United States Patent
Vogele et al.

(10) Patent No.: US 12,760,282 B2
(45) Date of Patent: Oct. 13, 2026

(54) METHOD FOR PRODUCING A MODIFIED BACTERIOPHAGE WITHOUT GENOME MODIFICATION

(71) Applicant: TECHNISCHE UNIVERSITÄT MÜNCHEN, Munich (DE)

(72) Inventors: Kilian Vogele, Raisting (DE); Friedrich Simmel, Munich (DE); Quirin Emslander, Erding (DE)

(73) Assignee: TECHNISCHE UNIVERSITÄT MÜNCHEN, Munich (DE)

( * ) Notice: Subject to any disclaimer, the term of this patent is extended or adjusted under 35 U.S.C. 154(b) by 1192 days.

(21) Appl. No.: 17/627,861

(22) PCT Filed: Jul. 16, 2020

(86) PCT No.: PCT/EP2020/070177
§ 371 (c)(1),
(2) Date: Jan. 18, 2022

(87) PCT Pub. No.: WO2021/009301
PCT Pub. Date: Jan. 21, 2021

(65) Prior Publication Data

US 2022/0259573 A1 Aug. 18, 2022

(30) Foreign Application Priority Data

Jul. 18, 2019 (EP) .................................... 19187079

(51) Int. Cl.

| | |
|---|---|
| ***A61K 35/76*** | (2015.01) |
| ***A61K 35/66*** | (2015.01) |
| ***A61P 31/04*** | (2006.01) |
| ***C12N 7/02*** | (2006.01) |
| ***C12N 15/01*** | (2006.01) |

(52) U.S. Cl.
CPC ................ *C12N 7/02* (2013.01); *A61K 35/76* (2013.01); *A61P 31/04* (2018.01); *C12N 15/01* (2013.01)

(58) Field of Classification Search
CPC ......... A61K 35/76; A61P 31/04; C12N 15/00; C12N 15/01; C12N 7/00
See application file for complete search history.

(56) References Cited

U.S. PATENT DOCUMENTS

2022/0259571 A1 8/2022 Vogele et al.

FOREIGN PATENT DOCUMENTS

| | | | |
|---|---|---|---|
| KR | 10-2013-0046158 | A | 5/2013 |
| WO | WO-02/07742 | A2 | 1/2002 |
| WO | WO-2021/009302 | A1 | 1/2021 |

OTHER PUBLICATIONS

Marks et al., "Bacteriophages and biotechnology: a review," Journal of Chemical Technology and Biotechnology. 75(1):6-17 (Jan. 2000).
Office Action for Chinese Patent Application No. 202080051654.0, dated Aug. 15, 2023 (15 pages).
Tong et al., "Clinical Diagnostics," Clinical Physician Training Series. Southeast University Press; Oct. 31, 2002; pp. 462-463.
Zhu et al., Gene Silencing—Principles and Methods. Yunnan Science and Technology Publishing House; Jul. 31, 2005; pp. 189-190 (6 pages).
Office Action for Chinese Patent Application No. 202080051900.2, dated Nov. 3, 2024 (30 pages).
Emslander et al., "Cell-free production of personalized therapeutic phages targeting multidrug-resistant bacteria," Cell Chem Biol. 29(9):1434-45 (Sep. 15, 2022).
Supplemental Information for Emslander et al., "Cell-free production of personalized therapeutic phages targeting multidrug-resistant bacteria," Cell Chem Biol. 29(9):1434-45 (Sep. 15, 2022).
Brown et al., "Phage engineering: how advances in molecular biology and synthetic biology are being utilized to enhance the therapeutic potential of bacteriophages," Quant Biol. 5(1):42-54 (2017).
Hagens et al., "Phages of Listeria offer novel tools for diagnostics and biocontrol," Front Microbiol. 5:159 (2014) (6 pages).
Kiro et al., "Efficient engineering of a bacteriophage genome using the type I-E CRISPR-Cas system," RNA Biol. 11(1):42-4 (2014).
Lu et al., "Dispersing biofilms with engineered enzymatic bacteriophage," Proc Natl Acad Sci U S A. 104(27):11197-202 (2007).
McNair et al., "PHANOTATE: a novel approach to gene identification in phage genomes," Bioinformatics. 35(22):4537-42 (Nov. 1, 2019).
Studier, "Bacteriophage T7," Science. 176(4033):367-76 (1972) (11 pages).
Studier, "Genetic analysis of non-essential bacteriophage T7 genes," J Mol Biol. 79(2):227-36 (1973).
International Search Report for International Patent Application No. PCT/EP2020/070177, mailed Oct. 1, 2020 (4 pages).
Kilcher et al., "Engineering Bacteriophages as Versatile Biologics," Trends Microbiol. 27(4):355- 367 (2019) (14 pages).
LMU, "What's going on in the Research Training Group Molecular Principles of Synthetic Biology," <https://www.grk2062.uni-muenchen.de/index.html>, Newsletter No. 1 2019 (2019) (8 pages).

(Continued)

*Primary Examiner* — Barry A Chestnut
(74) *Attorney, Agent, or Firm* — Clark & Elbing LLP

(57) ABSTRACT

The invention relates to a method for producing a modified bacteriophage in a cell-free expression system wherein the expression of at least one gene of interest is suppressed by a molecule specifically inhibiting its expression. The invention further relates to a composition and a kit for producing a modified bacteriophage. Moreover, the invention relates to a bacteriophage which is not modified on the genomic level but on the proteomic level and its use for therapy, for diagnostic and detection assays.

11 Claims, 4 Drawing Sheets

Figure 1:
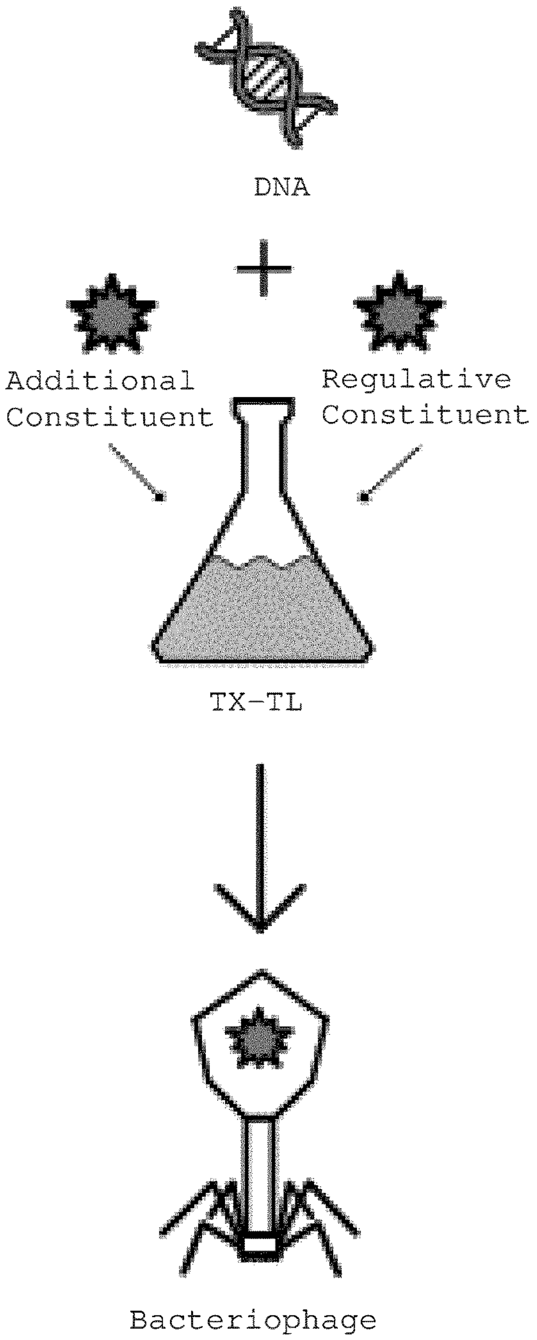

Specification includes a Sequence Listing.

(56) References Cited

OTHER PUBLICATIONS

Pires et al., "Genetically Engineered Phages: a Review of Advances over the Last Decade," Microbiol Mol Biol Rev. 80(3):523-43 (2016).
Tao et al., "Bacteriophage T4 nanoparticles for vaccine delivery against infectious diseases," Adv Drug Deliv Rev. 145:57-72 (2019).
Haq et al., "Bacteriophages and their implications on future biotechnology: a review," Virol J. 9:9 (2012) (8 pages).
Written Opinion of the International Searching Authority for International Patent Application No. PCT/EP2020/070177, mailed Oct. 1, 2020 (7 pages).
Barbu et al., "Phage Therapy in the Era of Synthetic Biology," Cold Spring Harb Perspect Biol. 8(10):a023879 (2016) (16 pages).
Bazan et al., "Phage display—a powerful technique for immunotherapy: 1. Introduction and potential of therapeutic applications," Hum Vaccin Immunother. 8(12):1817-28 (2012).
Bervoets et al., "A sigma factor toolbox for orthogonal gene expression in *Escherichia coli,*" Nucleic Acids Res. 46(4):2133-2144 (2018).
Esvelt et al., "A system for the continuous directed evolution of biomolecules," available in PMC Oct. 28, 2011, published in final edited form as: Nature. 472(7344):499-503 (2011) (18 pages).
Extended European Search Report for European Patent Application No. 19187079.9, dated Feb. 7, 2020 (9 pages).
Garamella et al., "The All *E. coli* TX-TL Toolbox 2.0: A Platform for Cell-Free Synthetic Biology," ACS Synth Biol. 5(4):344-55 (2016).
Hyman, "Phages for Phage Therapy: Isolation, Characterization, and Host Range Breadth," Pharmaceuticals (Basel). 12(1):35 (2019) (23 pages).
Pirnay et al., "The magistral phage," Viruses. 10(2):64 (2018) (7 pages).
Reyes et al., "Identifying Host Factors Associated with DNA Replicated During Virus Infection," Mol Cell Proteomics. 16(12):2079-97 (2017).
Rustad et al., "Cell-free TXTL synthesis of infectious bacteriophage T4 in a single test tube reaction," Synth Biol (Oxf). 3(1):ysy002 (2018) (7 pages).
Shimizu et al., "Cell-free translation reconstituted with purified components," Nat Biotechnol. 19(8):751-5 (2001) (6 pages).
Shin et al., "Genome replication, synthesis, and assembly of the bacteriophage T7 in a single cell-free reaction," pre-published version, published in final edited form as: ACS Synth Biol. 1(9):408-13 (2012) (6 pages).
Sun et al., "Protocols for implementing an Escherichia coli based TX-TL cell-free expression system for synthetic biology," J Vis Exp. (79):e50762 (2013) (14 pages).
Watabe et al.,"In vitro replication of bacteriophage phi 29 DNA," Proc Nat Acad Sci U S A. 79(17):5245-8 (Sep. 1982).
Homerova et al., "Optimization of a two-plasmid system for the identification of promoters recognized by RNA polymerase containing *Staphylococcus aureus* alternative sigma factor sigmaB," FEMS Microbiol Lett. 232(2):173-9. Mar. 2004. (8 pages).
Chauhan et al., "Reconstruction and topological characterization of the sigma factor regulatory network of Mycobacterium tuberculosis," Nat Commun. 7:11062 (Mar. 2016) (12 pages).
Gaida et al., "Expression of heterologous sigma factors enables functional screening of metagenomic and heterologous genomic libraries," Nat Commun. 6:7045 (May 2015) (10 pages).
Ceglarek et al., "A novel approach for separating bacteriophages from other bacteriophages using affinity chromatography and phage display," Sci. Rep., 3:3220 (Nov. 2013) (6 pages).
Bundy et al., "*Escherichia coli*-based cell-free synthesis of virus-like particles." Biotechnol Bioeng., 100(1):28-37. (May 2008).
Meijer and Salas, "Relevance of UP elements for three strong Bacillus subtilis phage $29 promoters," Nucleic Acids Research. 32(3):1166-1176 (Feb. 2004) (11 pages).
Van Nies et al., "Self-replication of DNA by its encoded proteins in liposome-based synthetic cells," Nature Communications. 9, 1583 (Apr. 2018) (12 pages).
Rustad et al., "Synthesis of Infectious Bacteriophages in an E. coli-based Cell-free Expression System," Journal of Visualized Experiments. 126 (Aug. 2017) (9 pages).

METHOD FOR PRODUCING A MODIFIED BACTERIOPHAGE WITHOUT GENOME MODIFICATION

FIELD OF THE INVENTION

The invention relates to a method for producing a modified bacteriophage in a cell-free expression system wherein the expression of at least one gene of interest is suppressed by a molecule specifically inhibiting its expression. The invention further relates to a composition and a kit for producing a modified bacteriophage. Moreover, the invention relates to a bacteriophage which is not modified on the genomic level but on the proteomic level and its use for therapy, for diagnostic and detection assays.

BACKGROUND OF THE INVENTION

Bacteriophages are viruses that specifically infect a host bacterium and multiply at the expense of that bacterium. The biotechnological applications of bacteriophages are very broad and range from evolution-based selection methods, such as the evolutionary improvement of the activity of enzymes (Esvelt et al. 2011), to the so-called phage display, which can be used to generate and optimize biological drugs such as therapeutic antibodies (Bazan et al. 2012), to the use of bacteriophages themselves as substitutes for antibiotics in bacteriophage therapy (Barbu et al. 2016). The latter is based on the natural ability of bacteriophages to attack and destroy specifically pathogenic bacteria (lysis). However, the development and production of phage-based therapeutics and diagnostics is still hampered by the difficulty of a simple and safe production method for bacteriophages. Until now, bacteriophages are produced by cultivation with the appropriate bacterium/pathogen (Pirnay et al., 2018). This requires compliance with the appropriate safety regulations for the respective bacteria, as well as the possibility to cultivate them. For dangerous pathogens handling is very difficult and costly due to the need of specially trained personnel in special facilities. The cell-free synthesis of proteins has a number of advantages over cellular expression, especially when toxic proteins are produced for the bacteria or non-natural amino acids are to be introduced into the proteins. Protein synthesis can be performed with the transcription and translation apparatus of lysed cells. After purification, the cell lysate is free of host DNA and enables the expression of the desired protein through the external addition of DNA. It is even possible to synthesize several proteins simultaneously or metabolites (Garamella et al. 2016). A number of cell-free expression systems are available, the composition of which can vary greatly. The so-called "PURE System" (Shimizu et al. 2001) consists of purified proteins, while crude cell extract of *E. coli* contains almost all intracellular proteins, including those that are not necessary for expression (Sun et al. 2013). In such a crude cell extract it has already been shown that it is possible to express infectious wild-type bacteriophages (Shin et al. 2012) as well as proteins (Garamella et al. 2016).

However, the development and production of phage-based therapeutics and diagnostics is currently still hampered by the difficulty of modifying bacteriophages. Genetic modification can, for example, increase the host area of a bacteriophage (Brown et al. 2017), improve the resolution of bacterial biofilms (Lu and Collins 2007), or introduce marker proteins for diagnostic purposes (Hagens and Loessner 2014). The classical approach for the modification of bacteriophages is "genome editing", which usually takes place via homologous recombination in the host bacterium. For this purpose, a DNA fragment with two homologous DNA sequences must be inserted, between which the DNA sequence to be inserted is located. Due to the sometimes very short infection time and other restrictions, only a very small part of the bacteriophages is altered—the recombination rate is only between $10^{-10}$ and $10^{-4}$—which makes extensive screening of the bacteriophages necessary (Pires et al. 2016). This approach can be further optimized by molecular biology approaches, such as a type I-E CRISPR-Cas system that attacks unmodified bacteriophages. However, due to a lack of experimental methods, it is not always possible to introduce a plasmid or DNA fragment into the host bacterium at all (Kiro et al. 2014). The complexity of the modification of bacteriophages is mainly due to the difficulty of changing the genome of bacteriophages. Another possibility to modify bacteriophages is to add the respective protein after a gene of the bacteriophage has been deleted. This is only possible with a limited number of capsid proteins, as the bacteriophages still have to assemble in the bacteria.

OBJECTIVES AND SUMMARY OF THE INVENTION

Therefore there is a need for a swift and less laborious general applicable method for the modification of bacteriophages without the modification of the genome of the bacteriophage.

To solve this problem, the inventors established an in vitro expression system in which the expression from the native genome of the bacteriophage is suppressed.

Thus, a first aspect of the invention refers to a method for producing a modified bacteriophage in a cell-free expression system comprising the steps of:

contacting a cell lysate of a microorganism with a genome of the bacteriophage, suppressing expression of at least one gene of interest encoded by the genome of the bacteriophage by adding a molecule specifically inhibiting the expression of the endogenous version of the at least one gene of interest.

Thus, for the described method it is not necessary to modify the genome of the bacteriophage. In other words, the invention refers to methods, compositions, and kits for producing bacteriophages containing a modification in the proteome level but not on the genome level.

The thereby produced bacteriophage does not represent a genetically modified organism (GMO), which is highly advantageous, since it may avoid hurdles in the authorization process of such bacteriophages for therapeutically purposes. Also, bacteriophages obtained by the provided method can be safely released into the environment as their modification is not passed on to the next generation of bacteriophages. Moreover, the gene expression in the cell free system avoids the cumbersome genetic modification of the genome of the bacteriophage.

Producing a "modified bacteriophage" as used herein refers to bacteriophages in which at least one gene of interest is suppressed (also termed knock down). Thus, the modification of the bacteriophage encompasses to knock-down of at least protein (without additional expression of a modified protein). In one embodiment, the term "modified bacteriophage" refers to a bacteriophage in which at least one gene of interest is suppressed. In one embodiment, the term "modified bacteriophage" refers to a bacteriophage in which one gene of interest is suppressed.

Such modified bacteriophages may be used for determining the function of the suppressed bacteriophage protein. Several commonly used enzymes are derived from bacteriophages, such as the T4 ligases or several RNA polymerases. Hence, the present method allows characterizing bacteriophage proteins based on knock-downs and functional assays. Alternatively, the bacteriophage could be modified in a way to alter host specificity. Bacteriophages may comprise different proteins each of which allow recognition of a different host. When knocking-down one of these proteins, the corresponding host can no longer be infected.

In specific embodiments, the modification encompasses the knock-down of a least one protein and the expression of a modified protein, in particular the expression of the modified version of the at least one protein of which the original version is suppressed.

Hence, in a specific embodiment, the method further comprises the step of expression of a modified version of the at least one gene of interest by adding a molecule encoding a modified version of the gene of interest. Alternatively or in addition, the method may comprise the step of adding a modified bacteriophage protein encoded by a modified version of the at least one gene of interest.

Thus, in some embodiments, a bacteriophage is produced having a genome which is not modified but comprises a modified bacteriophage protein.

Typically, the molecule specifically inhibiting the expression of the endogenous version is supressing the transcription or translation of the gene of interest. The molecule encoding a modified version of the gene of interest may be a nucleic acid molecule, such as a DNA or a RNA molecule. In preferred embodiments the DNA is in form of a plasmid or a PCR product.

In specific embodiments, the molecule specifically inhibiting the expression of the endogenous version of the gene of interest is a DNA molecule complementary to the sequence of the endogenous version of the gene of interest. For example, the molecule specifically inhibiting the expression of the endogenous version binds to the ribosome binding site of the gene of interest.

In exemplary embodiments, the gene of interest encodes the highly immunogeneic outer capsid protein (HOC). The HOC protein may have the sequence set out in SEQ ID NO: 1. Also sequences having a sequence which is at least 70%, at least 80%, at least 85% , at least 90%, at least 93%, at least 95%, at least 98% identical to SEQ ID NO: 1 are contemplated. Amino acid Sequence HOC (SEQ ID NO: 1;* represents stop codon/end of sequence):

```
MTFTVDITPKTPTGVIDETKQFTATPSGQTGGGTI

TYAWSVDNVPQDGAEATFSYVLKGPAGQKTIKVVA

TNTLSEGGPETAEATTTITVKNKTQTTTLAVTPAS

PAAGVIGTPVQFTAALASQPDGASATYQWYVDDSQ

VGGETNSTFSYTPTTSGVKRIKCVAQVTATDYDAL

SVTSNEVSLTVNKKTMNPQVTLTPPSINVQQDASA

TFTANVTGAPEEAQITYSWKKDSSPVEGSTNVYTV

DTSSVGSQTIEVTATVTAADYNPVTVTKTGNVTVT

AKVAPEPEGELPYVHPLPHRSSAYIWCGWWVMDEI
```

-continued

```
QKMTEEGKDWKTDDPDSKYYLHRYTLQKMMKDYPE

VDVQESRNGYIIHKTALETGIIYTYP*
```

The modified bacteriophage protein may comprise a modification selected from the group consisting of an affinity tag, a detection marker, a protein for the improvement of the bacteriophage or mutation or combinations thereof. For example, the modified bacteriophage protein may express a yellow fluorescent protein and a poly histidine tag. Such tags may allow purification and/or detection of the bacteriophage.

A protein for the improvement of the bacteriophage may be a biofilm degrading enzyme. In one embodiment, the biofilm degrading enzyme is a glycoside hydrolase, e.g. DspB. Such biofilm degrading enzyme increases access to biofilm forming bacteria.

In another embodiment, the modified bacteriophage protein comprises an enzyme, such as a luciferase. An accordingly modified bacteriophage could be used in a method to detect bacteria (e.g. *Listeria*) in food products. Advantageously, such method would allow an easy and fast detection of living bacteria by a simple luciferase assay.

The modified bacteriophage protein, e.g. a tail protein, a spike protein, a fiber protein or a baseplate protein, may also allow infecting a host that is different from the original host of the bacteriophage.

Further aspects of the invention relate to a composition and a kit for producing of a bacteriophage comprising:

a cell lysate of a microorganism, a genome of the bacteriophage, a molecule specifically inhibiting the expression of the endogenous version of the gene of interest. In preferred embodiments, the genome of the bacteriophage is not modified.

The composition and the kit may further comprise:

a molecule encoding a modified version of the gene of interest, and/or a modified bacteriophage protein encoded by a modified version of the at least one gene of interest.

Another aspect of the invention relates to a bacteriophage obtained by the method of the invention. A further aspect of the invention relates to a bacteriophage comprising a genome which is not modified, a modified bacteriophage protein.

Other aspect refer to the described bacteriophages for use as a medicament, for example for the treatment of a bacterial infection in a subject. The invention also contemplates the use of the described bacteriophage for avoiding bacterial growth in food or beverage, agriculture and for detecting for detecting specific microorganisms.

FIGURE LEGENDS

FIG. 1: Graphical overview of the Method for producing a modified bacteriophage without genome modification, including a DNA encoding the bacteriophage (DNA), a constituent that should be incorporated (additional constituent) and a constituent that regulates the transcription/translation of a protein of choice (regulative constituent).

Figure 2:
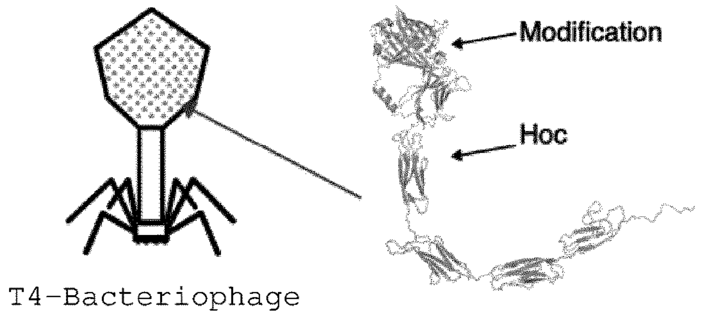
Figure 2:
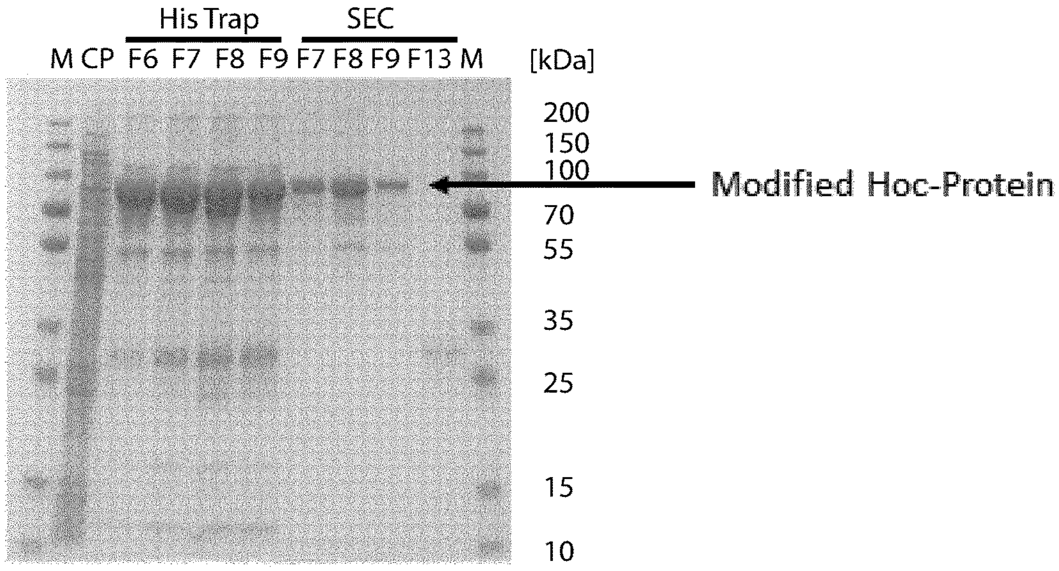

FIG. 2: Structural model of phage T4 (top left) with modification (YFP) fused with Hoc (top right). 12% SDS gel of several fractions of the His-YFP-Hoc protein which was purified via Histag and Size Exclusion Chromatography (bottom).

Figure 3:
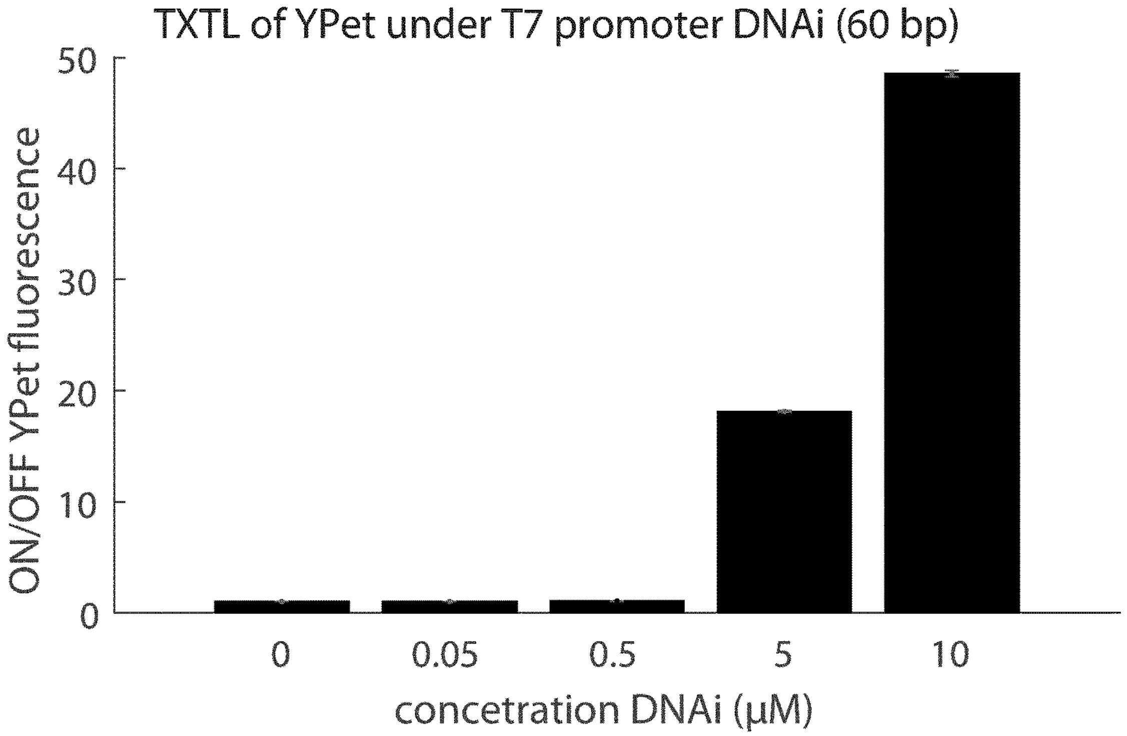

FIG. 3: On/off rations of the end levels of the fluorescence of a reporter protein in a cell-free reaction, in dependence of the added concertation of a single stranded DNA strand, which is complementary to the ribosome binding site of the mRNA encoding the reporter protein. The sequence of the single stranded DNA strand is

```
                              (SEQ ID NO: 2)
AGACATCTAGTtttctcctctttCTCATGAT

TAAACAAAATTATTTGTAGAGGCGCTTTC.
```

Figure 4:
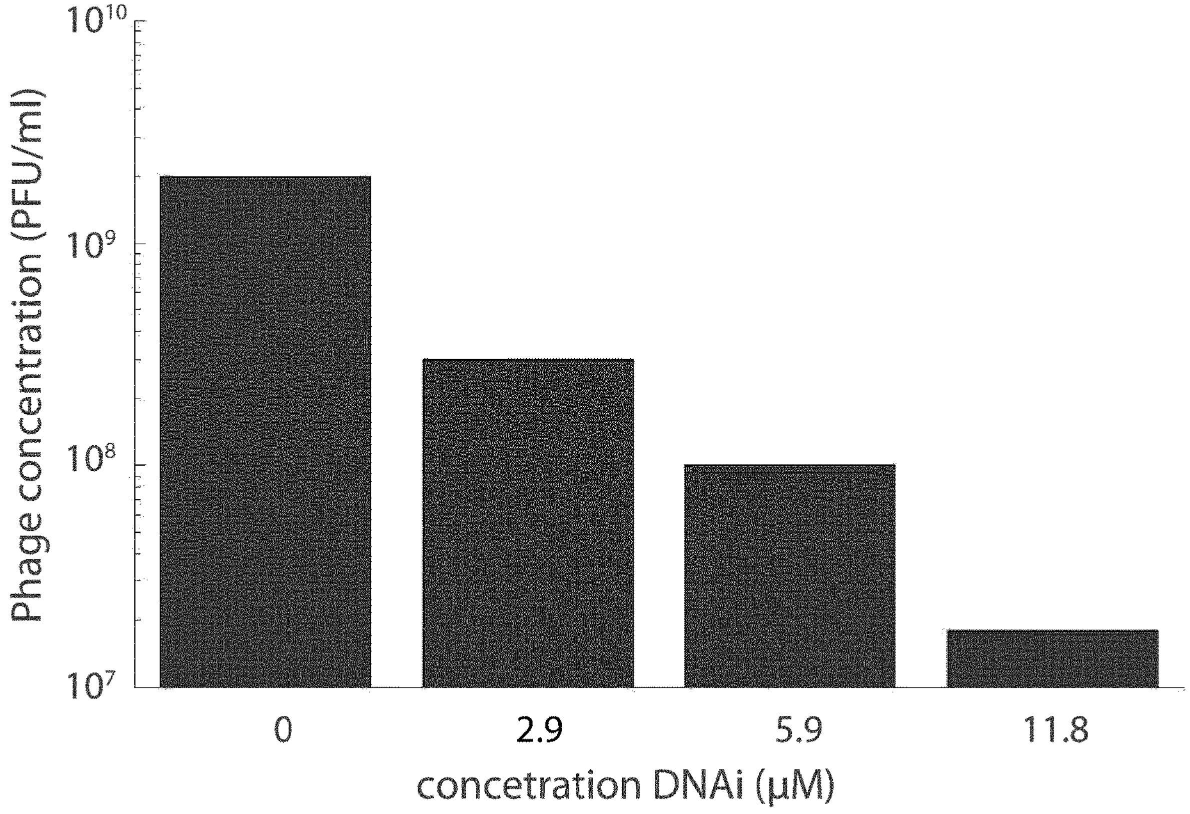

FIG. 4: Phage titers in a cell free reaction after phage expression in the dependents of the added single stranded DNA strand which is complementary to the ribosome binding site of the mRNA encoding the major capsid protein. The sequence of the single stranded DNA strand is

```
                              (SEQ ID NO: 3)
AGCCATATGTATATCTCCTTCTTAAAGTTAA

ACAAAATTATTTCTAGAGGGAAACCGTTG.
```

Figure 5:
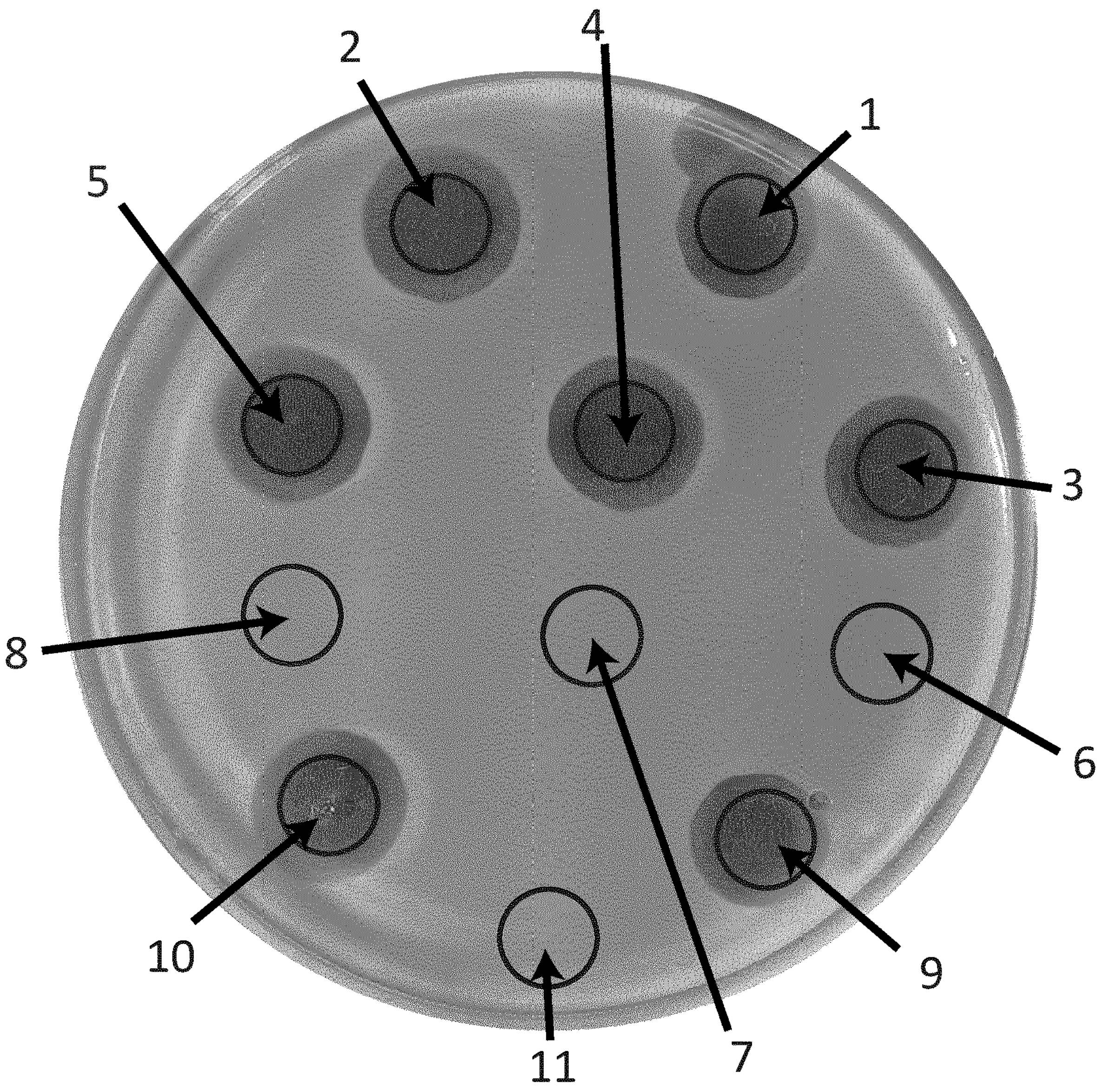

FIG. 5: Results of sport allay: spot 1: unpurified T7 Phage from the cell-free reaction, spot 2: first flow-through of the His-Tag column, spot 3: flow-through of the first washing step, spot 4: flow-through of the second washing step, spot 5: flow-through of the third washing step, spot 6: flow-through of the fourth washing step, spot 7: flow-through of the fifth washing step, spot 8: flow-through of the sixth washing step, spot 9: flow-through of the elution, spot 10: positive control from a T7 phage stock and spot 11: a negative control (elution buffer).

DETAILED DESCRIPTION OF THE INVENTION

Before the invention is described in detail with respect to some of its preferred embodiments, the following general definitions are provided.

The present invention as illustratively described in the following may suitably be practiced in the absence of any element or elements, limitation or limitations, not specifically disclosed herein.

The present invention will be described with respect to particular embodiments and with reference to certain figures but the invention is not limited thereto but only by the claims.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group which preferably consists only of these embodiments.

Where an indefinite or definite article is used when referring to a singular noun, e.g. "a", "an" or "the", this includes a plural of that noun unless something else is specifically stated. The terms "about" or "approximately" in the context of the present invention denote an interval of accuracy that the person skilled in the art will understand to still ensure the technical effect of the feature in question. The term typically indicates deviation from the indicated numerical value of ±10%, and preferably of ±5%.

Technical terms are used by their common sense. If a specific meaning is conveyed to certain terms, definitions of terms will be given in the following in the context of which the terms are used.

A first aspect of the invention refers to a method for producing a modified bacteriophage in a cell-free expression system comprising the steps of:

- contacting a cell lysate of a microorganism with a genome of the bacteriophage,
- suppressing expression of at least one gene of interest encoded by the genome of the bacteriophage by adding a molecule specifically inhibiting the expression of the endogenous version of the at least one gene of interest.

Thereby, the genome of the bacteriophage produced by the method is not modified during the production method. Thus, the modified version of the gene of interest will not be passed with a replication cycle that may occur after the method of the invention, e.g. in a host organism. Thereby the bacteriophage produced by the method of the invention differs from the bacteriophages produced by the classic modification of the bacteriophage genome, which passes the modification with all following replication cycles. Thus, bacteriophages produced by modifications of their genome are subject to high security criteria. On the contrary, the bacteriophages derived by the methods of the invention are not subject to the high security criteria.

In one embodiment, the gene of interest is a non-essential gene. A non-essential gene is a gene that is not essential for bacteriophage replication and/or phage assembly. Bacteriophage genomes are well characterized and there are various methods for carrying out such characterization (Studier 1972, Studier 1973, McNair et al. 2019).

A bacteriophage is a virus that infects bacteria or archaea. It is composed of capsid proteins that encapsulate a DNA or RNA genome. After infection of their genome into the cytoplasm, bacteriophages replicate in the microorganism using the transcription and translation apparatus of the bacterium. Phages are classified by the international Committee on Taxonomy of Viruses according to morphology and nucleic acid, including *Ackermannviridae, Myoviridae, Siphoviridae, Podoviridae, Lipothrixviridae, Rudiviridae, Ampullaviridae, Bicaudaviridae, Clavaviridae, Corticoviridae, Cystoviridae, Fuselloviridae, Globuloviridae, Inoviridae, Leviviridae, Microviridae, Plasmaviridae, Pleohpoviridae, Portogloboviridae, Spharohpoviridae, Spiraviridae, Tectiviridae, Tristromaviridae, Turriviridae*. The term "cell lysate" as used herein refers to a composition comprising the components of cells of a microorganism, in particular a bacterium, after lysis. The cell lysate is therefore void of intact cells, i.e. cell-free. Typically the cell lysate is free of host DNA. Preferably the cell lysate is free of host DNA and membranes. Moreover, the cell lysate may be free of small metabolites. The cell lysate comprises the transcription and translation machinery of the organism which is different to the host of the bacteriophage. In some embodiments, the term "free of" also includes "substantially free of".

Preferably the cell lysate is *E. coli* lysate. More preferably the cell lysate is *E. coli* Rosetta™(DE3) cell lysate.

The term "microorganism" refers to a bacterium or an archaeon. Preferably, the microorganism is a bacterium.

In a preferred embodiment, the method further comprises the step of expression of a modified version of the at least one gene of interest by adding a molecule encoding a modified version of the gene of interest. The molecule encoding a modified version of the gene of interest may be nucleotide sequence, in particular a DNA or RNA sequence. Preferably, the molecule encoding a modified version of the gene of interest may be a DNA sequence, such as a plasmid DNA.

Alternatively or in addition, the method further comprises the step of adding a modified bacteriophage protein encoded by a modified version of the at least one gene of interest. The modified bacteriophage protein may be present during the assembly of the bacteriophage.

In one embodiment, the gene of interest is a non-essential gene. In another embodiment, the gene of interest is an essential gene, e.g. one of the genes responsible for the capsid or one of the tail-fiber proteins and the method further comprises the step of adding a modified version of the essential gene. In yet another embodiment, the gene of interest is an essential gene and the method further comprises the step of adding a modified version of the protein corresponding to the essential gene.

Preferably, the genome of the bacteriophage contacted with the cell lysate is not modified. In other words, the genome of the bacteriophage is the native genome, i.e. the genome as isolated from the nature habitat. That means that the genome of the bacteriophage is not modified before and during the method for producing a modified bacteria, i.e. there is no active step of genome modification, such as gene deletion, addition of nucleotides, deletion of nucleotides or exchange of nucleotides. The skilled person understands that spontaneous modifications of the bacteriophage genome can occur.

In preferred embodiments, the gene of interest encodes a capsid protein or a tail fiber protein of the bacteriophage.

The molecule specifically inhibiting the expression, i.e. the expression inhibitor, of the endogenous version may suppress the transcription or translation of the gene of interest. For example the expression inhibitor may bind to the ribosome binding site of the gene of interest thereby inhibiting the translation of the gene of interest. The expression inhibitor may by a nucleotide sequence, a synthetic analogue thereof, a peptide or a small molecule specifically binding to site if inhibiting transcription or translation of the gene of interest.

Typically, the molecule encoding a modified version of the gene of interest is a nucleic acid molecule, for example a DNA or a RNA molecule.

Preferably, the molecule specifically inhibiting the expression of the endogenous version of the gene of interest is a nucleotide molecule, more preferably a DNA molecule complementary to the sequence to of the endogenous version of the gene of interest. The DNA may for example be provided in form of a plasmid or a PCR product.

In an exemplary embodiment, the gene of interest encodes highly immunogenic outer capsid protein (HOC).

The modified expression product may contain an affinity tag, a detection marker, a protein for the improvement of the bacteriophage or mutation or combinations thereof. The detection marker may be a fluorescent protein, such as yellow fluorescent protein (YFP). For example, the modified bacteriophage protein expresses a yellow fluorescent protein and a poly histidine Tag.

The method is useful for the generation of broad range bacteriophages. The bacteriophage may be selected from the family selected from the group of Ackermannviridae, Myoviridae, Siphoviridae, Podoviridae, Lipothrixviridae, Rudiviridae, Ampullaviridae, Bicaudaviridae, Clavaviridae, Corticoviridae, Cystoviridae, Fuselloviridae, Globuloviridae, Inoviridae, Leviviridae, Microviridae, Plasmaviridae, Pleolipoviridae, Portogloboviridae, Spharolipoviridae, Spiraviridae, Tectiviridae, Tristromaviridae and Turriviridae. In a preferred embodiment the bacteriophage from the family of Myoviridae, more preferably from the subfamily Tevenvirinae, even more preferably a T4virus, also termed T-even pages (containing Enterobacteria phage T2, Enterobacteria phage T4, Enterobacteria phage T6) most preferably the bacteriophage is *Escherichia* virus T4.

The genome of the bacteriophage may be provided in form of isolated native DNA, synthesized DNA, PCR product of the bacteriophage genome or a Yeast Artificial Chromosome.

The method may further comprise adding small metabolites and/or buffer.

Another aspect of the invention refers to a composition for producing of a bacteriophage comprising:

a cell lysate of a microorganism, a genome of the bacteriophage, a molecule specifically inhibiting the expression of the endogenous version of the gene of interest.

The composition may optionally comprises:

a molecule encoding a modified version of the gene of interest, and/or a modified bacteriophage protein encoded by a modified version of the at least one gene of interest.

In such a cell-free extract the bacteriophage can be produced by the use of the transcription and translation machinery of the microorganism from which the extract is derived from.

Typically the extract is derived from the host of the bacterium or is modified correspondingly.

Another aspect of the invention refers to a composition as described herein, wherein the genome of the bacteriophage is not modified.

Another aspect of the invention refers to a kit for producing a bacteriophage comprising:

a cell lysate of a microorganism, a genome of the bacteriophage, a molecule specifically inhibiting the expression of the endogenous version of the gene of interest.

Optionally, the kit further comprises a molecule encoding a modified version of the gene of interest, and/or a modified bacteriophage protein encoded by a modified version of the at least one gene of interest.

Another aspect of the invention refers to a bacteriophage comprising a genome which is not modified, modified bacteriophage protein.

In other words the invention refers to a bacteriophage which is modified on proteomic level but not on genomic level. The modified bacteriophage protein encompasses, that the bacteriophage is void of a protein of interest which is typically present in the unmodified version of the bacteriophage and optionally that the bacteriophage expresses a modified version of the protein of interest.

Another aspect of the invention refers to a bacteriophage obtained by the method as described herein. A further aspect of the invention refers to a bacteriophage as described herein for use as a medicament, for example for use in the treatment of a bacterial infection in a subject.

Other aspects of the invention refer to the use of the bacteriophage as described herein for avoiding bacterial growth in food or beverage and or for detecting specific microorganisms.

Experiments

Examples

Plasmid Preparation

TABLE 3

List of Primers for cloning and Sanger sequencing

| Primer | Sequence (5'-3') | Description |
|---|---|---|
| T4_f_left | AATTTTCCTTA TTAGGCCGCAA GGGCCTTCATA GTTTTAGCG (SEQ ID NO: 4) | Amplification of HOC gene from T4 genome |
| T4_r_right | ATGTACAATA TTAAATGCCT GACCAAAAAC GAACAAGCTG (SEQ ID NO: 5) | |
| pSB1C3_T7_ YPET_FWD | ATATCAACTG TAAAAGTCAT ACGACCCAGC GGCACCAGGT (SEQ ID NO: 6) | Generates overhang on the psb1C3 plasmid for Gibson assembly |
| pSB1C3_T7_ YPET_REV | TCATCTATAC CTATCCATAA AGCATGCCGG AGGAAACACA (SEQ ID NO: 7) | |
| HOC_YPET_ FWD | ACCTGGTGCC GCTGGGTCGT ATGACTTTTA CAGTTGATAT (SEQ ID NO: 8) | Generates overhang on HOC gene for Gibson assembly |
| HOC_YPED_ REV | GTTTCCTCCG GCATGCTTTA TGGATAGGTA TAGATG (SEQ ID NO: 9) | |
| His_before_ YFP_R3 | GAAAGAGGAG AAAACTAGAT GCATCATCAC (SEQ ID NO: 10) | Generates $His_6$ overhang, (phosphorylated) |
| His_before_ YFP_F2 | CATCACCACT CTAAAGGTGA AGAACTGTTT ACG (SEQ ID NO: 11) | |

Cloning

All listed oligonucleotides were designed with Benchling (USA). Secondary structure prediction was performed with Mfold (USA). All PCRs were prepared with the Q5 High-Fidelity 2× Master Mix kit (NEB, USA) according to Table 4 and 5 with Primers from Table 3. PCR settings were calculated with NEB Tm calculator (NEB, USA). The HOC coding sequence was cloned from the T4 phage (Table 2) in an expression vector (psbic3), which encodes YFP. The fusion of YFP HOC was extended with a Histag via overhang PCR. For transformation, plasmid amplification, protein expression and T4 propagation the *E.coli* cells from Table 1 were used.

DNA Preparation

Phage DNA was purified from previous prepared Phage stocks form titers above $10^8$ PFU/ml by phenol-chloroform extraction, followed by an ethanol precipitation. The concentration was adjusted to approximately 5 nM, determined by adsorption at 260 nm.

Cell Extract Preparation

For the generation of crude S30 cell extract a BL21-Rosetta 2(DE3) mid-log phase culture was bead-beaten with 0.1 mm glass beads in a Minilys homogenizer (Peqlab, Germany) as described in by Sun et al. (doi:10.3791/50762) The extract was incubated at 37° C. for 80 min to allow the digestion of genomic DNA, and was then dialyzed for 3 h at 4° C. with a cut-off of 10 kDa (Slide-A-Lyzer Dialysis Cassettes, Thermo Fisher Scientific). Protein concentration was estimated to be 30 mg/mL with a Bradford essay. The composite buffer contained 50 mM Hepes (pH 8), 5.5 mM ATP and GTP, 0.9 mM CTP and UTP, 0.5 mM dNTP, 0.2 mg/mL tRNA, 26 mM coenzyme A, 0.33 mM NAD, 0.75 mM cAMP, 68 mM folinic acid, 1 mM spermidine, 30 mM PEP, 1 mM DTT and 4.5% PEG-8000. As an energy source in this buffer phosphoenolpyruvate (PEP) was utilized instead of 3-phosphoglyceric acid (3-PGA). All components were stored at −80 ° C. before usage. A single cell-free reaction consisted of 42% (v/v) composite buffer, 25% (v/v) DNA plus additives and 33% (v/v) S30 cell extract. For ATP regeneration 13.3 mM maltose, against DNA degradation add 3.75 nM GamS and 1 U of T7 RNA polymerase (NEB, M0251S) were added to the reaction mix.

Phage Expression

For the phage expression 1nM of the phage genome was added and 1 nM of the Plasmid encoding the protein of interest regulated with a T7 promotor. The sample is incubated at 29 ° C. for the duration

Results

For producing a modified T4 bacteriophage expressing a modified highly immunogenic outer capsid protein (HOC protein) without genome modification the modified protein is needed e.g. on a plasmid or purified. The highly immunogenic outer capsid protein (HOC protein) was fused to a poly histidine tagged yellow fluorescent protein on a plasmid. Besides the phage DNA, the plasmid can further be co-expressed or the desired protein can be directly added to the cell-free expression system derived from *E.coli* (additional constituent). To reduce the translation of the native protein from the phage genome a regulative constituent DNAi is added (FIG. 1). In this case, the modified HOC was purified with a nickel chromatography followed by a size exclusion chromatography (FIG. 2). The impact of the DNAi was shown by reducing the translation of the fluorophore YPet under a T7 promotor in dependence of the DNAi concentration (FIG. 3). Also a reduction of in vitro expression of phages was measured in dependence of the DNAi concentration. Here translation of the major capsid protein was supressed by a single stranded DNA which is complementary to the ribosome binding site (FIG. 4).

Transient Modification with DNAi

For the transient modification, the T7 phages were assembled as before with the addition of 0.2 nM of a plasmid encoding major capsid protein of the T7 phage GlOB with a 3×GS Linker, a HiBiT-Tag and a 6×His-Tag (MLGV-ASTVAASPEEASVTSTEETLTPAQEAARTRAAN-KARKEAELAAATAEQGSGS GSVSGWRLFK-KISHHHHHH). To reduce the translation of the native GlOB protein from the phage genome a regulative constituent DNAi is added.

HisTag Purification

The phages were diluted to $10^6$ PFU/mL in 1×PBS and 20 mM imidazole after the assembly. The phage suspension was then applied onto Ni-NTA Agarose beads, which had been pre-equilibrated with a washing buffer containing 1×PBS and 20 mM imidazole. The column was subsequently washed with 6 column volumes of 1×PBS and 20 mM imidazole. The phages were eluted with one column volume of 1×PBS and 250 mM imidazole, before the titer was detected with a spot-assay.

Spot-Assay

For spot-assays 0.5% agarose NZCYM medium was melted and stored in a water bath at 48° C. 100 μL of overnight culture of the corresponding host bacterium was plated out with 4 ml of Agar. After the suspension solidified at RT the samples were added and the plates were incubated at 37° C. until plaques became visible (FIG. 5).

The application further contains the following items:

Item 1. Method for producing a modified bacteriophage in a cell-free expression system comprising the steps of:

- contacting a cell lysate of a microorganism with a genome of the bacteriophage,
- suppressing expression of at least one gene of interest encoded by the genome of the bacteriophage by adding a molecule specifically inhibiting the expression of the endogenous version of the at least one gene of interest.

Item 2. Method according to item 1, wherein the method further comprises the step of

- expression of a modified version of the at least one gene of interest by adding a molecule encoding a modified version of the gene of interest.

Item 3. Method according to item 1 or 2, wherein the method further comprises the step of

- adding a modified bacteriophage protein encoded by a modified version of the at least one gene of interest.

Item 4. Method according to any one of the preceding items, wherein the genome of the bacteriophage is not modified.

Item 5. Method according to any one of the preceding items, wherein the gene of interest encodes a capsid protein or a tail fiber protein of the bacteriophage.

Item 6. Method according to any one of the preceding items, wherein the molecule specifically inhibiting the expression of the endogenous version is supressing the transcription or translation of the gene of interest.

Item 7. Method according to any one of the preceding items, wherein the molecule specifically inhibiting the expression of the endogenous version binds to the ribosome binding site of the gene of interest.

Item 8. Method according to any one of the preceding items, wherein the molecule encoding a modified version of the gene of interest is a nucleic acid molecule.

Item 9. Method according to any one of the preceding items, wherein the molecule encoding a modified version of the gene of interest is a DNA or a RNA molecule.

Item 10. Method according to any one of the preceding items, wherein the molecule specifically inhibiting the expression of the endogenous version of the gene of interest is a nucleic acid molecule complementary to the sequence to of the endogenous version of the gene of interest.

Item 11. Method according to item 10, wherein the nucleic acid molecule is DNA, preferably in form of a plasmid or a PCR product.

Item 12. Method according to any one of the preceding items, wherein the gene of interest encodes highly immunogeneic outer capsid protein (HOC).

Item 13. Method according to any one of the preceding items, wherein the modified bacteriophage protein comprises a modification selected from the group consisting of an affinity tag, a detection marker, a protein for the improvement of the bacteriophage or mutation or combinations thereof.

Item 14. Method according to any one of the preceding items, wherein the modified bacteriophage protein expresses a yellow fluorescent protein and a poly histidine Tag.

Item 15. Method according to any one of the preceding items, wherein the bacteriophage a bacteriophage of the Myoviridae family, preferably of the Tevenvirinae subfamily, even more preferably a T4virus, most preferably the bacteriophage is *Echerichia* virus T4.

Item 16. Method according to any one of the preceding items, wherein the genome of the bacteriophage is provided in form of isolated native DNA, synthesized DNA, PCR product of the bacteriophage genome or a Yeast Artificial Chromosome.

Item 17. Method according to any one of the preceding items, wherein the method further comprises adding small metabolites.

Item 18. Composition for producing of a bacteriophage comprising:

- a cell lysate of a microorganism,
- a genome of the bacteriophage,
- a molecule specifically inhibiting the expression of the endogenous version of the gene of interest.

Item 19. Composition according to item 18, wherein the genome of the bacteriophage is not modified.

Item 20. Composition according to items 18 or 19, wherein the composition further comprises

- a molecule encoding a modified version of the gene of interest, and/or
- a modified bacteriophage protein encoded by a modified version of the at least one gene of interest.

Item 21. Kit for producing a bacteriophage comprising:

- a cell lysate of a microorganism,
- a genome of the bacteriophage, and/or
- a molecule specifically inhibiting the expression of the endogenous version of the gene of interest.

Item 22. Kit according to item 22, wherein the kit further comprises

- a molecule encoding a modified version of the gene of interest, and/or
- a modified bacteriophage protein encoded by a modified version of the at least one gene of interest.

Item 23. Bacteriophage comprising
a genome which is not modified,
modified bacteriophage protein.

Item 24. Bacteriophage obtained by the method according to item 1 and 17.

Item 25. Bacteriophage according to item 23 and 24 for use as a medicament.

Item 26. Bacteriophage according to item 23 and 24 for used in the treatment of a bacterial infection in a subject.

Item 27. Use of the bacteriophage according to item 23 and 24 for avoiding bacterial growth in food or beverage.

Item 28. Use of the bacteriophage of item 23 and 24 for detecting specific microorganisms.

Item 29. Method for producing a modified bacteriophage in a cell-free expression system comprising the steps of:
contacting a cell lysate of a microorganism with a genome of the bacteriophage,
suppressing expression of at least one gene of interest encoded by the genome of the bacteriophage by adding a molecule specifically inhibiting the expression of the endogenous version of the at least one gene of interest, wherein the gene of interest is a non-essential gene.

Item 30. Method for producing a modified bacteriophage in a cell-free expression system comprising the steps of:
contacting a cell lysate of a microorganism with a genome of the bacteriophage,
suppressing expression of at least one gene of interest encoded by the genome of the bacteriophage by adding a molecule specifically inhibiting the expression of the endogenous version of the at least one gene of interest, wherein the gene of interest is an essential gene.

Item 31. Method according to item 30, wherein the method further comprises the step of
expression of a modified version of the at least one gene of interest by adding a molecule encoding a modified version of the gene of interest.

Item 32. Method according to item 30, wherein the method further comprises the step of
adding a modified bacteriophage protein encoded by a modified version of the at least one gene of interest.

REFERENCES

Barbu et al. (2016): Phage Therapy in the Era of Synthetic Biology. In: Cold Spring Harbor perspectives in biology 8 (10).

Bazan et al. (2012): Phage display—a powerful technique for immunotherapy. 1. Introduction and potential of therapeutic applications. In: Human voaccines & immunotherapeutics 8 (12), s. 1817-1828.

Brown et al. (2017): Phage engineering. How advances in molecular biology and synthetic biology are berg utilized to enhance the therapeutic potential of bacteriophages. In: Quant Biol 5 (1), S. 42-54.

Esvelt et al. (2011): A System for the continuous directed evolution of biomolecules. In: Nature 472 (7344), S. 499-503. DOI:10.1038/nature09929.

Garamella et al. (2016): The All E. coli TX-TL Toolbox 2.0: A Platform for Cell-Free Synthetic Biology. In: ACS synthetic biology 5 (4), s. 344-355.

Hagens and Loessner (2014): Phages of Listeria offer novel tools for diagnostics and biocontrol. In: Frontiers in microbiology 5, 159.

Hyman et al. (2019): Phages for Phage Therapy: Isolation, Characterization, and Host Range Breadth. In: Pharmaceuticals 2019, 12(1), 35

Kiro et al (2014): Efficient engineering of a bacteriophage genome u sing the type I-E CRISPR-Cas System. In: RNA biology 11 (1), 42-44.

Lu and Collins (2007): Dispersing biofilms with engineered enzymatic bacteriophage. In: Proceedings of the National Academy of Sciences of the United States of America 104 (27), 11197-11202.

McNair et al (2019): Phanotate: a novel approach to gene identification in phage genomes. In: Bioinformatics 35 (22), 4537-4542.

Pires et al. (2016): Genetically Engineered Phages: a Review of Advances over the Last Decade. In: Microbiology and molecular biology reviews: MMBR 80 (3), S. 523-543.

Pirnay, et al. (2018). The magisterial phage. Viruses, 10(2), 64.

Shimizu, et al. (2001): Cell-free translation reconstituted with purified components. In: Nature biotechnology 19 (8), S. 751-755.

Shin, et al. (2012): Genome replication, Synthesis, and assembley of the bacteriophage T7 in a single cell-free reaction. In: ACS synthetic biology 1 (9), S. 408-413.

Studier (1972): Bacteriophage T7. In: Science 176 (4033), 367-376.

Studier (1973): Genetic analysis of non-essential bacteriophage T7 genes. In: Journal of Molecular Biology 79 (2), 227-236.

Sun, et al. (2013): Protocols for implementing an Escherichia coli base TX-TL cell-free expression System for synthetic biology. In: Journal of visualized experiments: JoVE (79), e50762.

Reyes et al (2017): Identifying Host Factors Associated with DNA Replicated During Virus Infection. In: Mol Cell Proteomics. 2017 Dec;16(12):2079-2097.

Rustad Cell-free TXTL synthesis of infectious bacteriophage T4 in a single test tube reaction Synthetic Biology, Volume 3, Issue 1.

The invention claimed is:

1. A method for producing a modified bacteriophage in a cell-free expression system comprising the steps of:

contacting a cell lysate of a microorganism with a genome of the bacteriophage; and suppressing expression of at least one gene of interest encoded by the genome of the bacteriophage by adding a molecule specifically inhibiting the expression of the endogenous version of the at least one gene of interest; and expressing a modified version of the at least one gene of interest by adding a molecule encoding a modified version of the gene of interest, and wherein the molecule inhibiting the expression of the endogenous version of the at least one gene of interest is a DNAi molecule binding to the ribosome binding side of the gene of interest, and wherein the DNAi molecule does not bind to the ribosome binding site of the modified version of the gene of interest.

2. The method according to claim 1, wherein the gene of interest is an essential gene or a non-essential gene.

3. The method according to claim 1, wherein the genome of the bacteriophage is not modified.

4. The method according to claim 1, wherein the gene of interest encodes a capsid protein or a tail fiber protein of the bacteriophage.

5. The method according to claim 1, wherein the modified bacteriophage protein comprises a modification selected from the group consisting of an affinity tag, a detection marker, a protein for the improvement of the bacteriophage or mutation or combinations thereof.

6. The method according to claim 1, wherein the bacteriophage is a bacteriophage of the Myoviridae family.

7. A composition for carrying out the method of claim 1 comprising:

a cell lysate of a microorganism; and a genome of the bacteriophage; and a molecule specifically inhibiting the expression of the endogenous version of the gene of interest; and a molecule encoding a modified version of the gene of interest, and wherein the molecule inhibiting the expression of the endogenous version of the at least one gene of interest is a DNAi molecule binding to the ribosome binding side of the gene of interest, and wherein the DNAi molecule does not bind to the ribosome binding site of the modified version of the gene of interest.

8. A kit for carrying out the method of claim 1 comprising:

a cell lysate of a microorganism; and a genome of the bacteriophage; and a molecule specifically inhibiting the expression of the endogenous version of the gene of interest; and a molecule encoding a modified version of the gene of interest, and wherein the molecule inhibiting the expression of the endogenous version of the at least one gene of interest is a DNAi molecule binding to the ribosome binding side of the gene of interest, and wherein the DNAi molecule does not bind to the ribosome binding site of the modified version of the gene of interest.

9. The method of claim 4, wherein the gene of interest encodes a highly immunogeneic outer capsid protein (HOC).

10. The method of claim 6, wherein the bacteriophage is of the Tevenvirinae subfamily.

11. The method of claim 10, wherein the bacteriophage is *Escherichia* virus T4.

* * * * *

SEQUENCE LISTING

```
<160> NUMBER OF SEQ ID NOS: 11

<210> SEQ ID NO 1
<211> LENGTH: 376
<212> TYPE: PRT
<213> ORGANISM: Bacteriophage T4

<400> SEQUENCE: 1

Met Thr Phe Thr Val Asp Ile Thr Pro Lys Thr Pro Thr Gly Val Ile
1               5                   10                  15

Asp Glu Thr Lys Gln Phe Thr Ala Thr Pro Ser Gly Gln Thr Gly Gly
```

```
            20                  25                  30

Gly Thr Ile Thr Tyr Ala Trp Ser Val Asp Asn Val Pro Gln Asp Gly
        35                  40                  45

Ala Glu Ala Thr Phe Ser Tyr Val Leu Lys Gly Pro Ala Gly Gln Lys
    50                  55                  60

Thr Ile Lys Val Val Ala Thr Asn Thr Leu Ser Glu Gly Gly Pro Glu
65                  70                  75                  80

Thr Ala Glu Ala Thr Thr Thr Ile Thr Val Lys Asn Lys Thr Gln Thr
                85                  90                  95

Thr Thr Leu Ala Val Thr Pro Ala Ser Pro Ala Ala Gly Val Ile Gly
            100                 105                 110

Thr Pro Val Gln Phe Thr Ala Ala Leu Ala Ser Gln Pro Asp Gly Ala
        115                 120                 125

Ser Ala Thr Tyr Gln Trp Tyr Val Asp Asp Ser Gln Val Gly Gly Glu
    130                 135                 140

Thr Asn Ser Thr Phe Ser Tyr Thr Pro Thr Thr Ser Gly Val Lys Arg
145                 150                 155                 160

Ile Lys Cys Val Ala Gln Val Thr Ala Thr Asp Tyr Asp Ala Leu Ser
                165                 170                 175

Val Thr Ser Asn Glu Val Ser Leu Thr Val Asn Lys Lys Thr Met Asn
            180                 185                 190

Pro Gln Val Thr Leu Thr Pro Pro Ser Ile Asn Val Gln Gln Asp Ala
        195                 200                 205

Ser Ala Thr Phe Thr Ala Asn Val Thr Gly Ala Pro Glu Glu Ala Gln
    210                 215                 220

Ile Thr Tyr Ser Trp Lys Lys Asp Ser Ser Pro Val Glu Gly Ser Thr
225                 230                 235                 240

Asn Val Tyr Thr Val Asp Thr Ser Ser Val Gly Ser Gln Thr Ile Glu
                245                 250                 255

Val Thr Ala Thr Val Thr Ala Ala Asp Tyr Asn Pro Val Thr Val Thr
            260                 265                 270

Lys Thr Gly Asn Val Thr Val Thr Ala Lys Val Ala Pro Glu Pro Glu
        275                 280                 285

Gly Glu Leu Pro Tyr Val His Pro Leu Pro His Arg Ser Ser Ala Tyr
    290                 295                 300

Ile Trp Cys Gly Trp Trp Val Met Asp Glu Ile Gln Lys Met Thr Glu
305                 310                 315                 320

Glu Gly Lys Asp Trp Lys Thr Asp Asp Pro Asp Ser Lys Tyr Tyr Leu
                325                 330                 335

His Arg Tyr Thr Leu Gln Lys Met Met Lys Asp Tyr Pro Glu Val Asp
            340                 345                 350

Val Gln Glu Ser Arg Asn Gly Tyr Ile Ile His Lys Thr Ala Leu Glu
        355                 360                 365

Thr Gly Ile Ile Tyr Thr Tyr Pro
    370                 375


<210> SEQ ID NO 2
<211> LENGTH: 60
<212> TYPE: DNA
<213> ORGANISM: Artificial Sequence
<220> FEATURE:
<223> OTHER INFORMATION: complementary to the ribosome binding site of
      the mRNA encoding the reporter protein

<400> SEQUENCE: 2
```

-continued agacatctag ttttctcctc tttctcatga ttaaacaaaa ttatttgtag aggcgctttc 60

<210> SEQ ID NO 3
<211> LENGTH: 60
<212> TYPE: DNA
<213> ORGANISM: Artificial Sequence
<220> FEATURE:
<223> OTHER INFORMATION: complementary to the ribosome binding site of the mRNA encoding the major capsid protein

<400> SEQUENCE: 3
agccatatgt atatctcctt cttaaagtta aacaaaatta tttctagagg gaaaccgttg 60

<210> SEQ ID NO 4
<211> LENGTH: 42
<212> TYPE: DNA
<213> ORGANISM: Artificial Sequence
<220> FEATURE:
<223> OTHER INFORMATION: T4_f_left

<400> SEQUENCE: 4
aattttcctt attaggccgc aagggccttc atagttttag cg 42

<210> SEQ ID NO 5
<211> LENGTH: 40
<212> TYPE: DNA
<213> ORGANISM: Artificial Sequence
<220> FEATURE:
<223> OTHER INFORMATION: T4_r_right

<400> SEQUENCE: 5
atgtacaata ttaaatgcct gaccaaaaac gaacaagctg 40

<210> SEQ ID NO 6
<211> LENGTH: 40
<212> TYPE: DNA
<213> ORGANISM: Artificial Sequence
<220> FEATURE:
<223> OTHER INFORMATION: pSB1C3_T7_YPET_FWD

<400> SEQUENCE: 6
atatcaactg taaaagtcat acgacccagc ggcaccaggt 40

<210> SEQ ID NO 7
<211> LENGTH: 40
<212> TYPE: DNA
<213> ORGANISM: Artificial Sequence
<220> FEATURE:
<223> OTHER INFORMATION: pSB1C3_T7_YPET_REV

<400> SEQUENCE: 7
tcatctatac ctatccataa agcatgccgg aggaaacaca 40

<210> SEQ ID NO 8
<211> LENGTH: 40
<212> TYPE: DNA
<213> ORGANISM: Artificial Sequence
<220> FEATURE:
<223> OTHER INFORMATION: HOC_YPET_FWD

<400> SEQUENCE: 8
acctggtgcc gctgggtcgt atgactttta cagttgatat 40

<210> SEQ ID NO 9
<211> LENGTH: 36
<212> TYPE: DNA

-continued

```
<213> ORGANISM: Artificial Sequence
<220> FEATURE:
<223> OTHER INFORMATION: HOC_YPED_REV

<400> SEQUENCE: 9

gtttcctccg gcatgcttta tggataggta tagatg                            36


<210> SEQ ID NO 10
<211> LENGTH: 30
<212> TYPE: DNA
<213> ORGANISM: Artificial Sequence
<220> FEATURE:
<223> OTHER INFORMATION: His_before_YFP_R3

<400> SEQUENCE: 10

gaaagaggag aaaactagat gcatcatcac                                   30


<210> SEQ ID NO 11
<211> LENGTH: 33
<212> TYPE: DNA
<213> ORGANISM: Artificial Sequence
<220> FEATURE:
<223> OTHER INFORMATION: His_before_YFP_F2

<400> SEQUENCE: 11

catcaccact ctaaaggtga agaactgttt acg                               33
```